(12) United States Patent
Gonzalez et al.

(10) Patent No.: US 11,123,516 B2
(45) Date of Patent: Sep. 21, 2021

(54) CATHETERS INCLUDING RADIOPAQUE MARKERS AND METHODS OF MAKING THE SAME

(71) Applicant: Medtronic Minimed, Inc., Minneapolis, MN (US)

(72) Inventors: Juan Ramon Gonzalez, Arleta, CA (US); Sam William Bowman, Valencia, CA (US); Rudolph A. Montalvo, Woodland Hills, CA (US)

(73) Assignee: Medtronic Minimed, Inc., Minneapolis, MN (US)

( * ) Notice: Subject to any disclaimer, the term of this patent is extended or adjusted under 35 U.S.C. 154(b) by 119 days.

(21) Appl. No.: 16/041,542

(22) Filed: Jul. 20, 2018

(65) Prior Publication Data

US 2019/0022352 A1    Jan. 24, 2019

Related U.S. Application Data

(60) Provisional application No. 62/535,796, filed on Jul. 21, 2017.

(51) Int. Cl.

| | | |
|---|---|---|
| *A61M 25/01* | (2006.01) | |
| *A61M 25/00* | (2006.01) | |
| *A61L 29/14* | (2006.01) | |
| *A61L 29/06* | (2006.01) | |
| *A61L 29/18* | (2006.01) | |

(Continued)

(52) U.S. Cl.
CPC ......... *A61M 25/0012* (2013.01); *A61L 29/06* (2013.01); *A61L 29/14* (2013.01); *A61L 29/18* (2013.01); *A61M 25/0069* (2013.01); *A61M 5/14276* (2013.01); *A61M 25/0102* (2013.01); *A61M 25/0108* (2013.01); *A61M 2205/32* (2013.01); *A61M 2207/00* (2013.01); *B29C 45/14336* (2013.01); *B29K 2083/00* (2013.01); *B29K 2105/0097* (2013.01); *B29K 2683/00* (2013.01); *B29L 2031/7542* (2013.01)

(58) Field of Classification Search
CPC .......... A61M 25/0012; A61M 25/0069; A61M 25/0108; A61M 2205/32
See application file for complete search history.

(56) References Cited

U.S. PATENT DOCUMENTS

| | | | |
|---|---|---|---|
| 4,445,896 A | | 5/1984 | Gianturco |
| 4,531,943 A | * | 7/1985 | Van Tassel ........ A61M 25/0069 600/435 |

(Continued)

FOREIGN PATENT DOCUMENTS

| | | |
|---|---|---|
| CA | 2382871 A1 | 3/2001 |
| WO | WO 97/16154 A1 | 5/1997 |

(Continued)

OTHER PUBLICATIONS

PCT International Search and Written Opinion dated Nov. 11, 2018 for PCT App. Ser. No. PCT/US2018/043147.

(Continued)

*Primary Examiner* — Laura A Bouchelle
(74) *Attorney, Agent, or Firm* — Henricks Slavin LLP (57) ABSTRACT

A catheter including a tubular catheter body defining a distal portion, a distal end and a lumen that extends to the distal end, a radiopaque marker carried within the lumen, and a non-metal tip that is bonded to distal end of the catheter body.

22 Claims, 6 Drawing Sheets

(51) Int. Cl.
    *B29K 683/00*  (2006.01)
    *B29K 105/00*  (2006.01)
    *B29L 31/00*  (2006.01)
    *B29K 83/00*  (2006.01)
    *B29C 45/14*  (2006.01)
    *A61M 5/142*  (2006.01)

(56) References Cited

U.S. PATENT DOCUMENTS

| | | | |
|---|---|---|---|
| 4,577,637 A | | 3/1986 | Mueller, Jr. |
| 5,256,158 A | * | 10/1993 | Tolkoff ............... A61B 6/12 604/529 |
| 6,093,180 A | * | 7/2000 | Elsberry ............ A61M 25/001 128/898 |
| 8,323,268 B2 | * | 12/2012 | Ring ............... A61M 5/16854 604/891.1 |
| 2010/0076407 A1 | | 3/2010 | Ring |
| 2013/0296903 A1 | | 11/2013 | Nita |
| 2015/0174364 A1 | * | 6/2015 | Kennelly ......... A61M 25/0053 604/527 |
| 2015/0216620 A1 | * | 8/2015 | Davies ............... A61B 18/1492 606/41 |

FOREIGN PATENT DOCUMENTS

| WO | WO 97/48435 | 12/1997 |
| WO | WO 2009/012362 A1 | 1/2009 |
| WO | WO 2009/070682 A1 | 6/2009 |

OTHER PUBLICATIONS

Extended European Search Report dated May 18, 2021 for EPO App. Ser. No. 18835465.8.

* cited by examiner

CATHETERS INCLUDING RADIOPAQUE MARKERS AND METHODS OF MAKING THE SAME

CROSS-REFERENCE TO RELATED APPLICATIONS

This application claims the benefit of U.S. Provisional Application No. 62/535,796, filed Jul. 21, 2017, which is incorporated herein by reference.

BACKGROUND

1. Field of Inventions

The present inventions relate generally to catheters that may be used to, for example, deliver medication to bodily regions such as the subarachnoid space and other intrathecal spaces, the peritoneum, and various subcutaneous areas.

2. Description of the Related Art

Implantable infusion systems have been used to provide patients with a medication or other substance (collectively "infusible substance") and frequently include a catheter and an implantable infusion device with a reservoir and a fluid transfer device. The reservoir stores the infusible substance and, in some instances, implantable infusion devices are provided with a fill port that allows the reservoir to be transcutaneously filled (and/or re-filled) with a hypodermic needle. The reservoir is coupled to the fluid transfer device which is, in turn, connected to an outlet port. The catheter includes at least one outlet and may be connected to the outlet port. As such, the infusible substance may be transferred from the reservoir to the target body region by way of the fluid transfer device and the catheter.

The delivery of infusible substance into the subarachnoid space around the spinal cord or brain, for example, requires the use of catheters that are relatively long, thin and soft. While such mechanical properties are necessary and useful, they result in catheters that lack the structural rigidity required for the insertion process. As such, a stylet may be temporarily positioned within the catheter lumen and used to push the distal portion of the catheter to the target location. The distal portion of the catheter frequently includes the fluid outlet(s) and, accordingly, the distal portion also includes a visualization marker that may be observed through the use of suitable instrumentalities so that the fluid outlet(s) may be precisely positioned. In particular, the marker may be in the form of a radiopaque marker tip that is mounted on the distal end of the catheter and that may be observed through the use of a fluoroscope.

Figure 1:
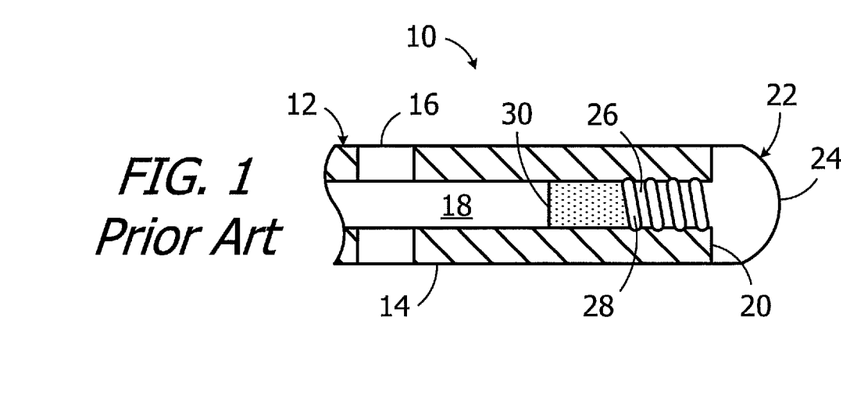
FIG. 1 is a partial section view of the distal portion of a conventional catheter.

One example of a conventional catheter that may be inserted into the subarachnoid space is generally represented by reference numeral 10 in FIG. 1. The catheter 10 includes a catheter body 12, formed from a polymer such as silicone, with a distal portion 14 having apertures 16 and a central lumen 18 that extends from the proximal end of the catheter to the distal end 20. A radiopaque marker tip 22, formed from platinum-iridium alloy, is carried on the distal end 20 of the catheter body 12. The marker tip 22 includes a main portion 24 and a connector 26 that is located within the central lumen 18, and may be secured to the catheter body distal portion with a polymeric adhesive. The connector 26 may have threads 28 (or the like) to help secure the marker tip 22 to the catheter body 12. In some instances, a silicone plug 30 is positioned within the central lumen 18 proximal of the marker tip 22. During positioning, the stylet engages the marker tip (or silicone plug, if present) and pushes the distal portion of the catheter by applying force to the proximal end of the marker tip (or silicone plug, if present).

The present inventors have determined that although the catheter illustrated in FIG. 1 is an advance in the art, it is susceptible to improvement. For example, it is difficult to reliably secure a metal marker tip to the distal end of a catheter that is soft and thin. In particular, platinum and other noble metals do not easily form oxides and, as a result, do not reliably bond to the polymeric adhesives. Thus, although the polymeric adhesive bonds well to a polymeric catheter body, the polymeric adhesive does not bond well to the platinum-iridium marker tip.

SUMMARY

A catheter in accordance with one implementation of a present invention includes a tubular catheter body defining a distal portion, a distal end and a lumen that extends to the distal end, a radiopaque marker carried within the lumen, and a non-metal tip that is bonded to distal end of the catheter body. The present inventions also include systems having such a catheter in combination with an implantable infusion device.

A method in accordance with one implementation of a present invention includes the steps of inserting a radiopaque marker into a lumen of a catheter body that defines a distal end, and after the radiopaque marker has been inserted into the catheter body lumen, molding a tip onto the distal end of the catheter body.

A method in accordance with one implementation of a present invention includes the steps of inserting a radiopaque marker into a lumen of a catheter body that defines a distal end, and after the radiopaque marker has been inserted into the catheter body lumen, securing a non-metal tip to the distal end of the catheter body with adhesive.

There are a number of advantages associated with the present apparatus and methods. Most notably, the present apparatus and methods facilitate the use of tip materials that will create a better bond between the tip and the catheter body, thereby reducing the likelihood that the tip will separate from the catheter body.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions are also not limited to the exemplary implantable infusion devices described herein and, instead, are applicable to other implantable, external, or otherwise ambulatory infusion devices that currently exist or are yet to be developed. Additionally, although the present inventions are discussed in the exemplary context of subarachnoid catheters, the present inventions are also applicable to other intrathecal catheters as well as other catheters including, but not limited to, peritoneal catheters and subcutaneous catheters.

Figure 2:
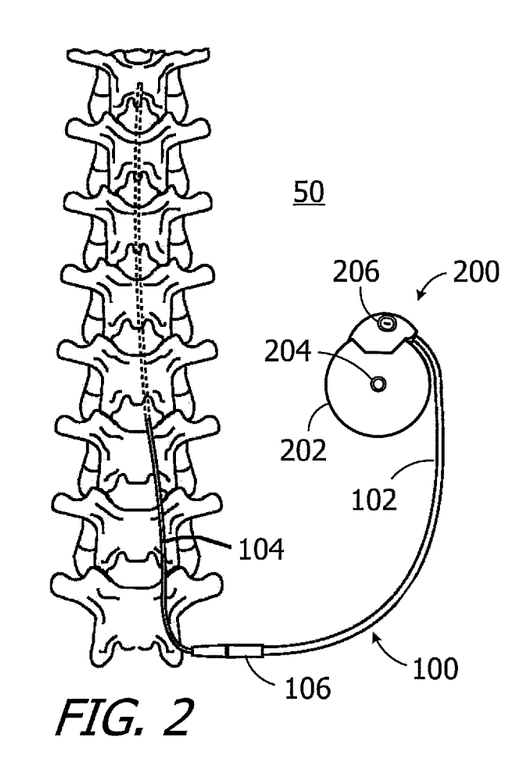
FIG. 2 is a representation of a catheter apparatus in accordance with one embodiment of a present invention that is located within the subarachnoid space and that is connected to an implantable infusion device.

One example of an implantable infusion system in accordance with a present invention is generally represented by reference numeral 50 in FIG. 2. The implantable infusion system 50 includes a catheter apparatus 100 and an implantable infusion device 200. The catheter apparatus 100 includes a proximal catheter 102 that is connected to the implantable infusion device 200, a subarachnoid catheter 104, which is discussed in greater detail below with reference to FIGS. 4A-4B, and a connector assembly 106. The implantable infusion device 200 includes a housing 202 in which an infusible substance reservoir, a fluid transfer device, control electronics, and various other devices are carried. An outlet port (not shown) connects the proximal catheter 102 to the implantable infusion device 200. The implantable infusion device 200 also includes a fill port 204 that allows the reservoir to be transcutaneously filled (and/or re-filled) with a hypodermic needle. A side port 206, which is connected to a passageway between the outlet of the fluid transfer device and the outlet port, facilitates access to the implanted catheter 100, typically by way of a hypodermic needle. Although the present inventions are not limited to any particular type of implantable infusion device, exemplary implantable infusion devices are described in U.S. Pat. No. 8,251,860, which is incorporated herein by reference.

Figure 3:
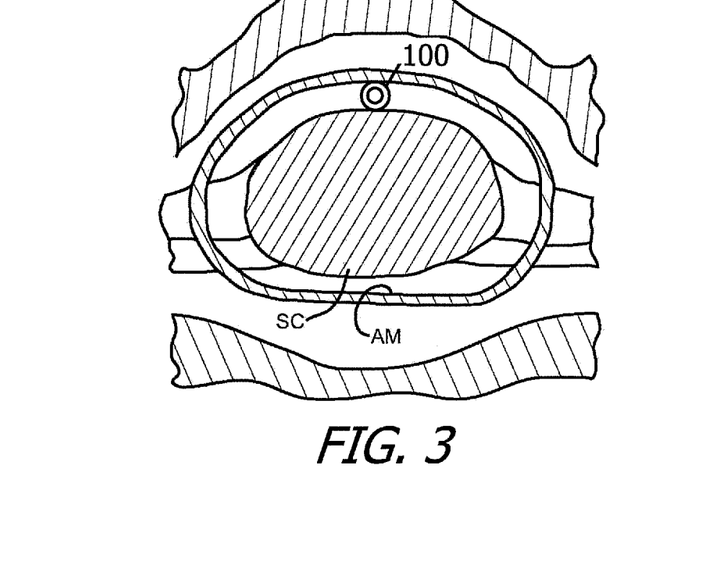
FIG. 3 is a section view of the catheter illustrated in FIG. 2 located within the subarachnoid space.

The connector assembly 106 may be used to connect the proximal catheter 102 to the subarachnoid catheter 104 after the subarachnoid catheter has been positioned within the patient's body. For example, in those instances where a stylet is used to push the distal portion of the subarachnoid catheter 104 to the target location, the subarachnoid catheter will be connected to the proximal catheter 102 after the stylet has been removed. The infusible substance may then be delivered to, for example, the portion of the subarachnoid space along the spine between the spinal cord SC and the arachnoid mater AM, as is illustrated in FIG. 3.

Figure 4A:
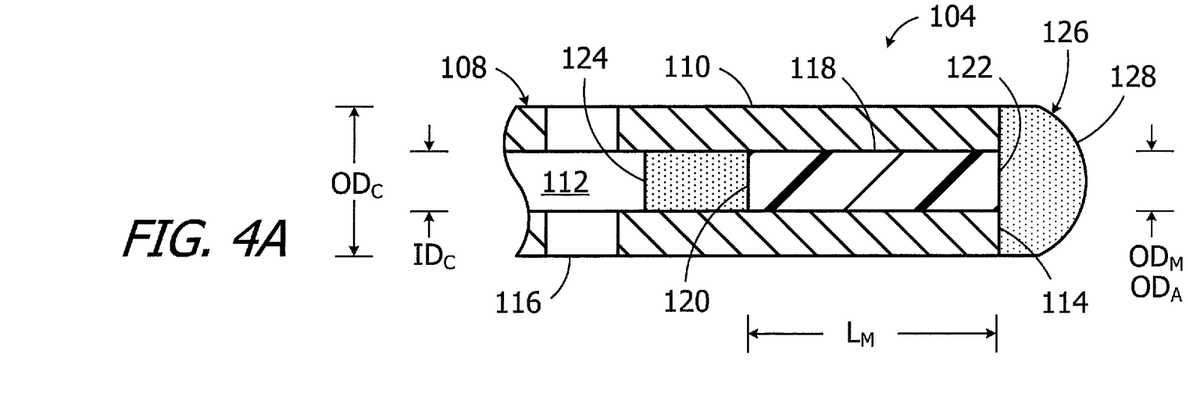
FIG. 4A is a section view of the distal portion of the catheter illustrated in FIG. 2.

Turning to FIG. 4A, the exemplary subarachnoid catheter 104 includes a catheter body 108 with a distal portion 110 and a central lumen 112 that extends from the proximal end of the catheter (i.e. the end adjacent to the connector assembly 106 in FIG. 2) to the distal end 114 of the catheter body. The catheter distal portion 110 includes a plurality of apertures 116 that extend from the exterior of the distal portion to the central lumen 112. The apertures 116 may be any suitable number, size and shape. In at least some implementations, the apertures 116 may be offset longitudinally and/or circumferentially along portions of the catheter body.

Although the present catheters are not so limited, the exemplary subarachnoid catheter 104 is formed from thermoset silicone with a hardness of about 70 Shore A. As used herein in the context of hardness, the word "about" means±5%. The hardness may range from about 65 to about 75 Shore A. Materials that may be employed in other implementations include, but are not limited to other thermoset materials such as thermoset polyurethane within the aforementioned hardness range. Thermoplastic materials thermoplastic polyurethane, polyethylene, polypropylene, polytetrafluoroethylene, and polyvinylchloride (PVC), may be employed, although such materials may be coated with silicone for biocompatibility reasons. To that end, exemplary multi-layer catheters may include a two-layer catheter with silicone on outside and polyethylene on the inside. In other instances, especially those not intended for intrathecal use, a three-layer catheter with an inner polyethylene layer, an outer PVC layer, and in intermediate polyvinyl alcohol layer may be employed.

With respect to dimensions, the exemplary catheter body 108, which is configured for use in the subarachnoid space, is circular in cross-section and has an outer diameter $OD_C$ of about 0.054 to 0.056 inches and an inner diameter $ID_C$ (defined by the central lumen 112) of about 0.020 to 0.022 inches. The present catheters are not, however, limited to a circular cross-sectional shape. The length of the catheter body 112 may also vary from about 10 inches to about 40 inches, depending on the intended application.

A radiopaque marker 118 is located within the central lumen 112 in the distal portion 110 of the catheter body 108. The exemplary radiopaque marker 118 is a cylindrical structure having proximal and distal ends 120 and 122. Suitable materials for the marker 118 include, but are not limited to, radiopaque noble metals such as platinum, platinum-iridium, gold, and palladium. The radiopaque marker 118 has an outer diameter $OD_M$ that is equal to the catheter body inner diameter $ID_C$, i.e., about 0.0175 to 0.0195 inches. The marker outer diameter $OD_M$ may also be about 0.001 to 0.003 inches greater than the inner diameter $ID_C$ of the catheter body prior the marker 118 to being inserted into the central lumen 112. Here, the central lumen 112 (and the inner diameter $ID_C$) will expand to accommodate the marker 118. The length $L_M$ of the marker 118 may about 0.075 to 0.095 inches. The distal end 122 of the exemplary marker 118 does not extend beyond the catheter body distal end 114. Nor are there any other structures distal of the catheter body distal end 114 that are formed from radiopaque metal such as platinum, platinum-iridium, gold, and palladium.

The exemplary subarachnoid catheter 104 may, in some instances, also be provided with an abutment 124 that is located within the central lumen 112 proximal to the radiopaque marker 118. The exemplary abutment 124, which is cylindrical in shape and has an outer diameter $OD_A$ that is equal to, or is about 0.001 to 0.003 inches greater than, the inner diameter inner diameter $ID_C$ of the catheter body 108. The abutment 124 may be formed by, for example, injecting a hardenable material into the central lumen 112. Suitable hardenable materials include, for example, adhesives such as silicone adhesives (e.g., MED-1137 silicone adhesive from NuSil Technology) and silicone polymers such as liquid silicone rubber (LSR). The abutment 124 prevents the stylet from directly engaging the radiopaque marker 118 and transfers the force from the stylet to the catheter body distal portion 110 instead of the radiopaque marker 118. As a result, abutment 124 reduces the likelihood that the stylet will separate the radiopaque marker 118 from the distal portion of the catheter body 108 as the stylet is pushing the distal portion 110 of the catheter to a target location within, for example, the subarachnoid space around the spinal cord.

A non-metal tip 126 (FIG. 4A), which is not part of or formed from the same material as the radiopaque marker 118, is located on the distal end 114 of the catheter body 108. The exemplary tip 126 may be configured such that the tip covers the entire surface area if the distal end 114, as shown, and has a curved distal end 128. In other embodiments, the tip may cover slightly less than the entire surface area and/or have a differently shaped distal end.

Figure 4B:
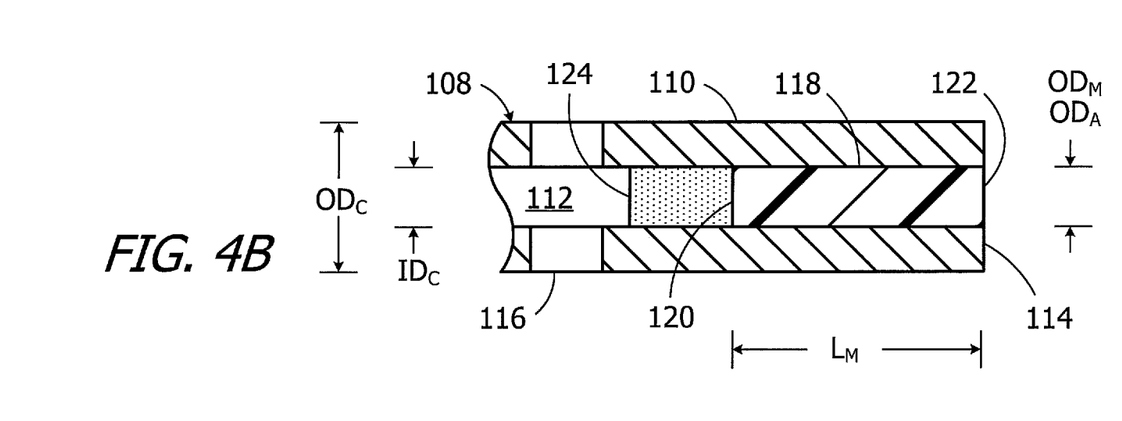
FIG. 4B is a section view of part of the distal portion of the catheter illustrated in FIG. 2.

A wide variety of tips, tip materials, and tip manufacturing techniques may be employed. Referring first to the exemplary catheter 104 illustrated in FIG. 4A, the radiopaque marker 118 is inserted into the central lumen 112 prior to the formation of the catheter tip 126, as shown in FIG. 4B. The abutment 124 (if present) may be formed prior to the formation of the catheter tip 126 (as shown) or after the formation of the catheter tip. After the radiopaque marker 118 has been inserted into the central lumen 112, a material (hereafter "tip material") other than the material from which the catheter is formed may be molded or otherwise deposited onto the distal end 114 of the catheter body 108 through the use of an insert molding process or other suitable process. For example, the tip material may be a silicone adhesive, such as MED-1137 silicone adhesive from NuSil Technology, or a silicone molding compound such as LSR or high consistency rubber. The tip material may also be softer that the catheter body material in some implementations. For example, in those instances where the catheter body 108 is formed from material with a hardness of about 70 Shore A, the hardness of the silicone molding compound may range from less than 70 Shore A to 30 Shore A or less. Suitable silicone adhesives with hardnesses of less than 70 Shore A include those with a hardness of 30 Shore A. The softer material results in tip that is less traumatic to tissue than would be a tip formed from metal or from the same material as the catheter body. It should also be noted here that the present silicone molding compounds are thermoset materials, i.e., materials that cannot be re-melted, as is the silicone catheter body material.

The silicone adhesive and silicone molding compound will both bond better to the silicone catheter than will a noble metal (such as platinum, platinum-iridium, gold, and palladium) because they are chemically similar to the silicone catheter material. All three are silicone polymers. As a result of the superior bond between the catheter body and the catheter tip, the present catheter tip is less likely to become separated from the catheter body than would a conventional metal tip.

Figure 5A:
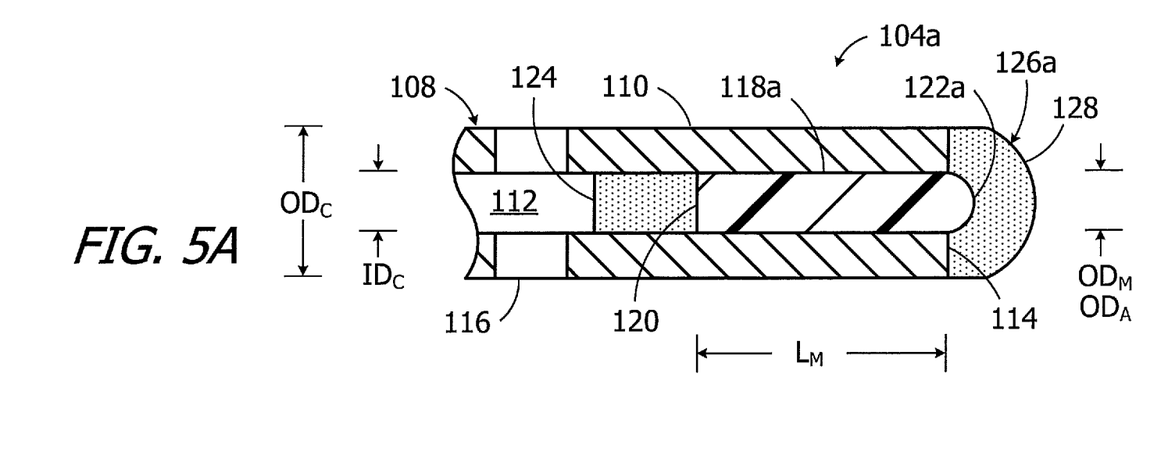
FIG. 5A is a section view of the distal portion of a catheter in accordance with one embodiment of a present invention.

Another exemplary subarachnoid catheter is generally represented by reference numeral 104*a* in FIG. 5A. The catheter 104*a* is substantially similar to catheter 104 and similar elements are represented by similar reference numerals. Here, however, the radiopaque marker 118*a* includes a curved distal end 122*a* that extends beyond the distal end 114 of the catheter body 108. The tip 126*a*, which may be formed from the same materials as the tip 126, includes an indentation that accommodates the curved distal end 122*a*.

Figure 5B:
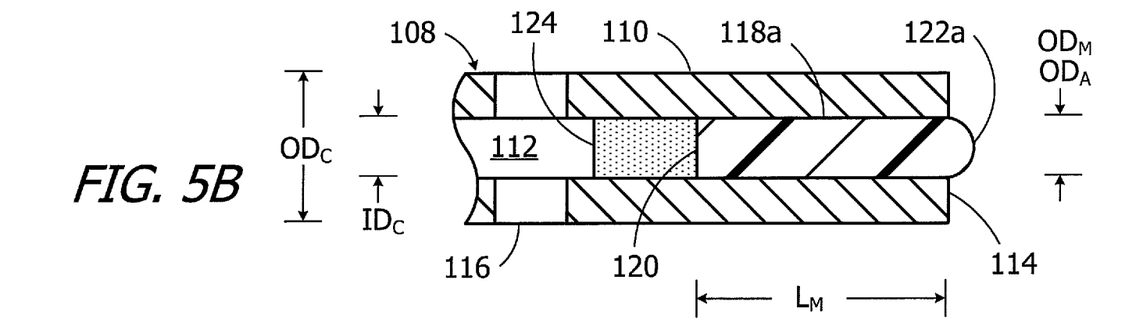
FIG. 5B is a section view of part of the distal portion of a catheter in accordance with one embodiment of a present invention.

Here too, the radiopaque marker 118*a* is inserted into the central lumen 112 prior to the formation of the catheter tip, as shown in FIG. 5B, and the abutment 124 (if present) may be formed prior to the formation of the catheter tip 126*a* (as shown) or after the formation of the catheter tip. The tip material, which is discussed above with reference to FIGS. 4A and 4B, may be molded or otherwise deposited onto the distal end 114 of the catheter body 108 after the radiopaque marker 118*a* has been inserted into the central lumen 112.

Figure 6A:
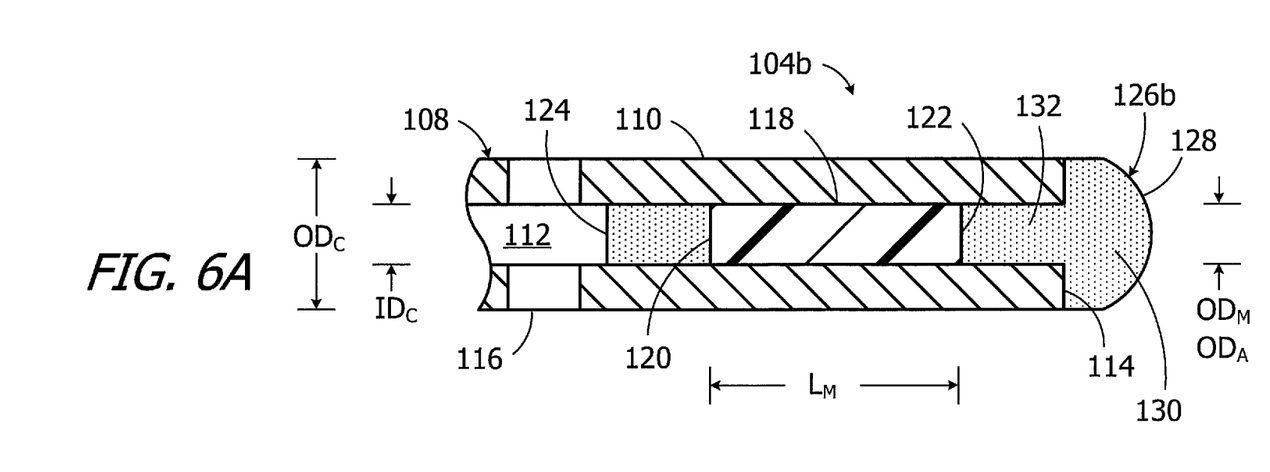
FIG. 6A is a section view of the distal portion of a catheter in accordance with one embodiment of a present invention.

The exemplary subarachnoid catheter generally represented by reference numeral 104*b* in FIG. 6A is substantially similar to catheter 104 and similar elements are represented by similar reference numerals. Here, however, the location of the radiopaque marker 118 results in the distal end 122 being located proximal of the distal end 114 of the catheter body 108. The volume between the radiopaque marker distal end 122 and the catheter body distal end 114 is occupied by a portion of the tip 126*b*. In particular, the tip 126*b* includes a main portion 130 and a connector 132, and may be formed from the same materials as the tip 126. The main portion 130 is identical in size, shape and functionality to the tip 126. The connector 132, which is located within the central lumen 112, increases the bonding surface area between the tip 126*b* and the catheter body 108, as compared to the tip 126, thereby creating a stronger bond.

Figure 6B:
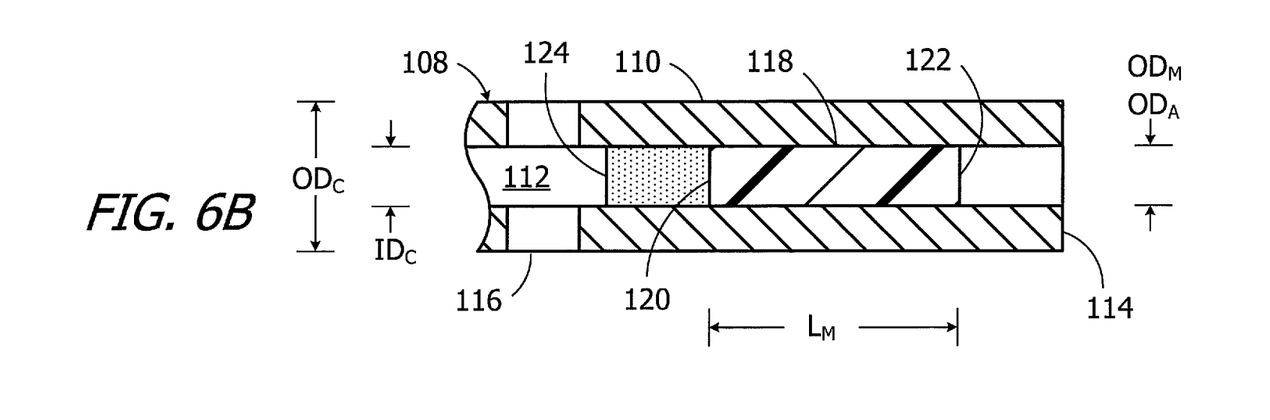
FIG. 6B is a section view of part of the distal portion of a catheter in accordance with one embodiment of a present invention.

With respect to manufacturing, and referring to FIG. 6B, the radiopaque marker 118 is inserted into the central lumen 112 prior to the formation of the catheter tip such that the marker distal end 122 is proximal of the catheter body distal end 114. The abutment 124 (if present) may, as noted above, be formed prior to the formation of the catheter tip 126*b* (as shown) or after the formation of the catheter tip. The tip material, which is discussed above with reference to FIGS. 4A and 4B, may be molded or otherwise deposited onto the surface that defines the central lumen 112 of the catheter body 108, and onto the distal end 114, after the radiopaque marker 118 has been inserted into the central lumen.

Figure 7A:
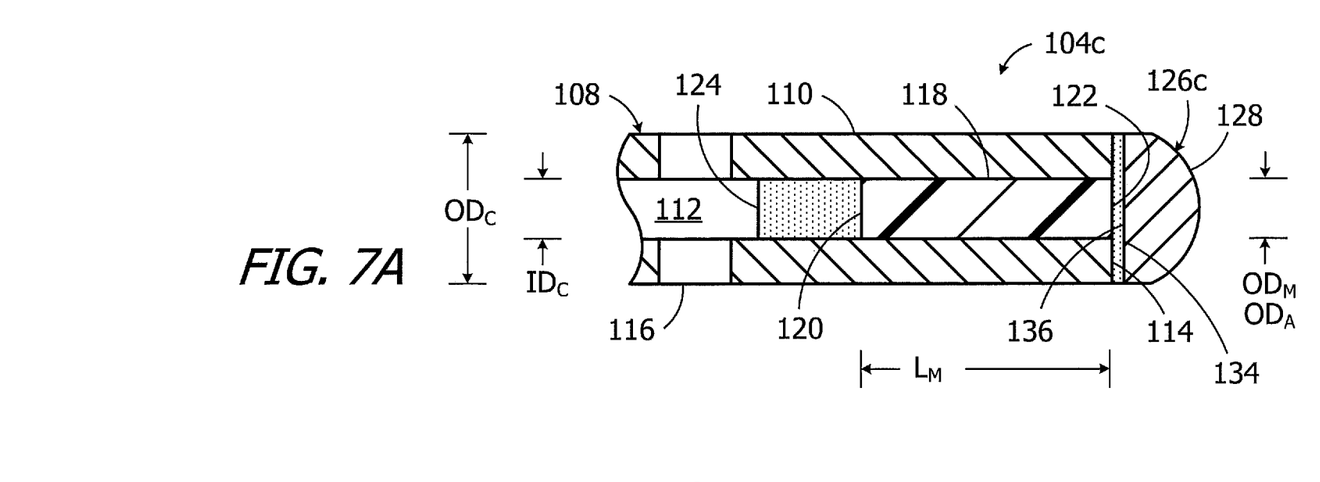
FIG. 7A is a section view of the distal portion of a catheter in accordance with one embodiment of a present invention.

Still another exemplary subarachnoid catheter is generally represented by reference numeral 104*c* in FIG. 7A. The catheter 104*c* is substantially similar to catheter 104 and similar elements are represented by similar reference numerals. Here, however, the tip 126*c* is a pre-formed non-metallic tip that is secured to the distal end 114 of the catheter body 108 and to the distal end 122 of the marker 118 with a layer of adhesive 134, such as the silicone adhesives described above, that bonds well to the catheter body. In addition to the curved distal end 128, the tip 126*c* has a flat proximal end 136 that is adjacent to the catheter body distal end 114 and the radiopaque marker distal end 122. In other implementations, non-metallic tips that are secured to the catheter body distal end 114 with adhesive may have a shape similar to that of the tip 126*b* (FIG. 6A).

Figure 7B:
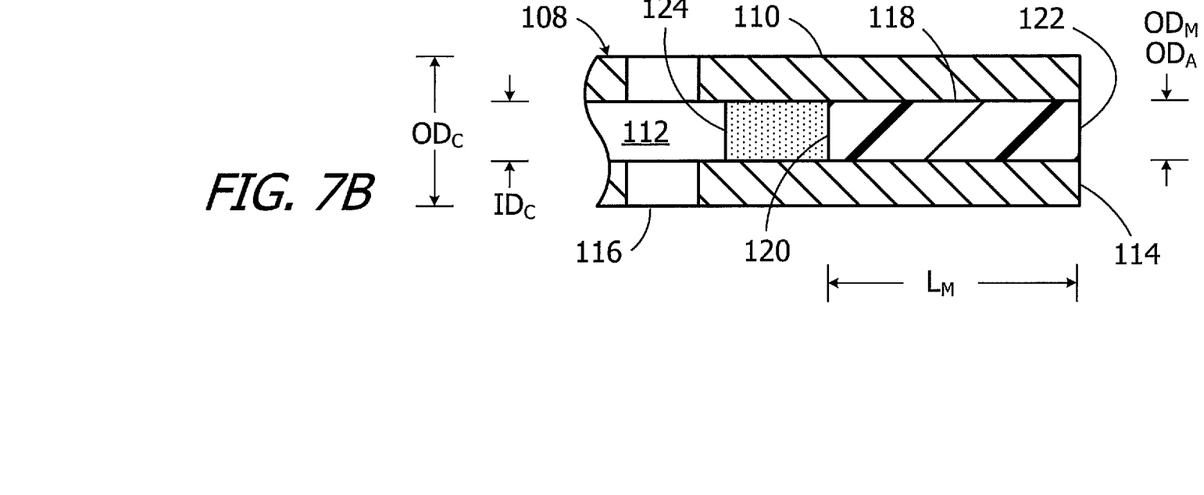
FIG. 7B is a section view of part of the distal portion of a catheter in accordance with one embodiment of a present invention.

Turning to FIG. 7B, the radiopaque marker 118 may be inserted into the central lumen 112 prior to the tip 126*c* being secured to the catheter body distal end 114. The abutment 124 (if present) may, as noted above, be formed before (as shown) or after the catheter tip 126c has been adhered to the catheter body distal end 114. The tip 126c may be secured to the catheter body distal end 114 with adhesive 134 after the radiopaque marker 118 has been inserted into the central lumen.

Figure 8A:
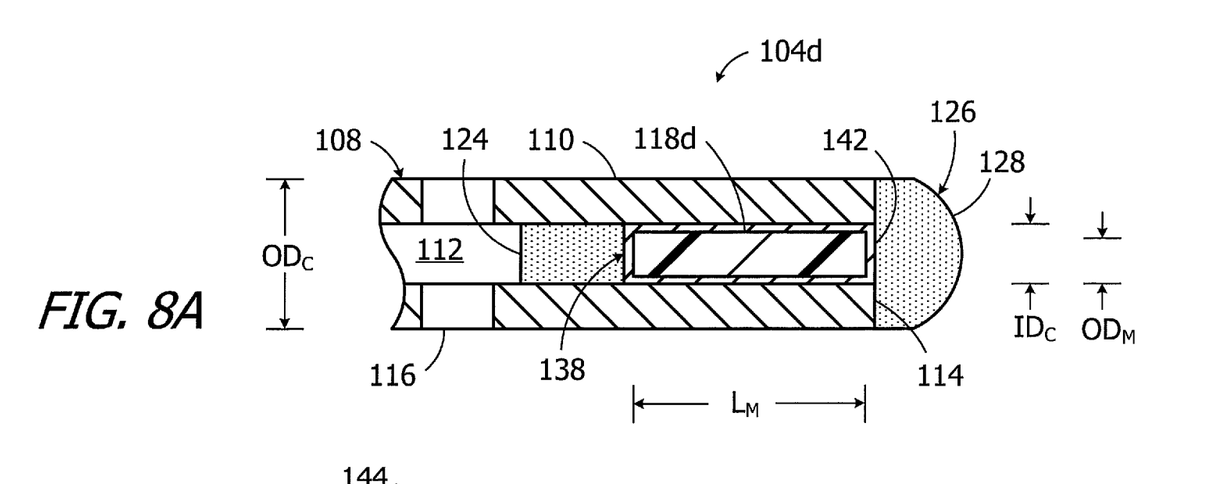
FIG. 8A is a section view of the distal portion of a catheter in accordance with one embodiment of a present invention.

The exemplary subarachnoid catheter generally represented by reference numeral 104d in FIG. 8A is substantially similar to catheter 104 and similar elements are represented by similar reference numerals. Here, however, outer diameter ON of the radiopaque marker 118d is slightly less than the inner diameter $ID_C$ of the catheter body 108. The radiopaque marker 118d is encased (or at least substantially encased) in silicone shell 138 with a proximal end 140 that is proximal of the radiopaque marker proximal end 120 and a distal end 142 that is distal of the radiopaque marker distal end 122. The silicone shell 138, which may be formed from a silicone adhesive or a silicone molding compound, will bond to the catheter body 108 in the manner described above. A thin coating of silane primer may be applied to the marker 118d prior to the application of the silicone shell. The silicone shell distal end 142 also increases the silicone surface area to which the tip 126 is bonded as compared to, for example, the catheter illustrated in FIG. 4A, thereby increasing the strength of the bond between the tip and the remainder of the catheter.

Figure 8B:
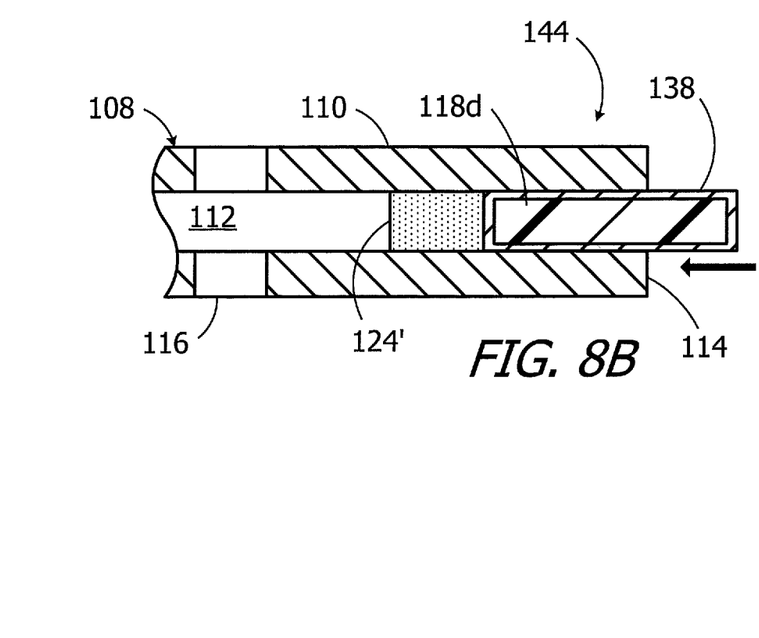
FIG. 8B is a section view showing the assembly of part of the distal portion of a catheter in accordance with one embodiment of a present invention.
Figure 8C:
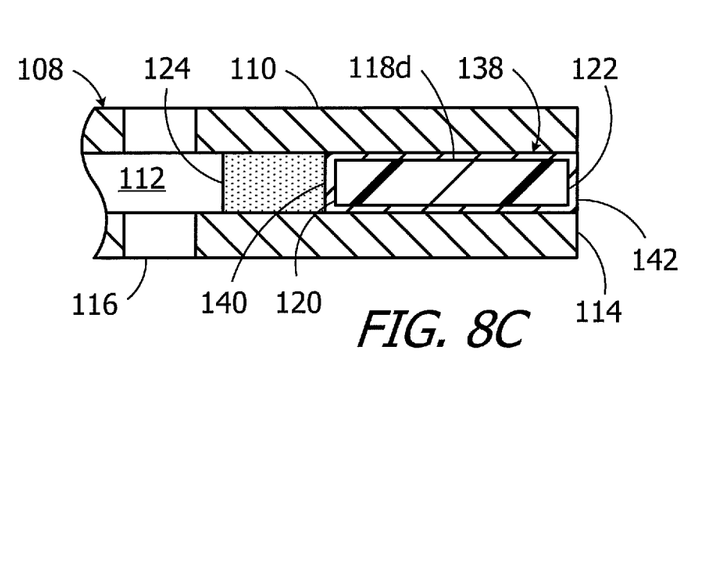
FIG. 8C is a section view of part of the distal portion of a catheter in accordance with one embodiment of a present invention.

Referring to FIG. 8B, the radiopaque marker 118d may be encased in the silicone shell 138 prior to insertion into the central lumen 112 and then inserted into the central lumen prior to the formation of the catheter tip. A small volume of silicone adhesive or silicone molding compound 124' may be applied to the surface of the central lumen 112 prior to insertion of the encased marker 118d. The silicone adhesive or silicone molding compound 124' will be pushed proximally and, once hardened, will form the abutment 124. A small amount of the silicone adhesive or silicone molding compound may also remain between the surface of the lumen 112 and the outer surface of the silicone shell 138. Next, tip material such as that discussed above with reference to FIGS. 4A and 4B may be molded or otherwise deposited onto the catheter body distal end 114 and the silicone shell distal end 142 (FIG. 8A).

Although the inventions disclosed herein have been described in terms of the preferred embodiments above, numerous modifications and/or additions to the above-described preferred embodiments would be readily apparent to one skilled in the art. By way of example, but not limitation, the present inventions are applicable to catheters that supply stimulation energy, as opposed to or in addition to, infusible substances. Such catheters are sometimes referred to a spinal cord stimulation leads. It is intended that the scope of the present inventions extend to all such modifications and/or additions and that the scope of the present inventions is limited solely by the claims set forth below.

We claim:

1. A catheter, comprising:
a tubular catheter body formed from a silicone thermoset material and defining a size and a shape that facilitates insertion into an intrathecal space and including a distal portion, a distal end and a surface that defines a lumen that extends to the distal end;
a radiopaque marker carried within the lumen inward of the surface that defines the lumen; and
a non-metal tip, formed from a different silicone thermoset material than the catheter body silicone thermoset material, bonded to the distal end of the catheter body.

2. A catheter as claimed in claim 1, wherein
the catheter body silicone thermoset material has a first hardness; and
the tip silicone thermoset material has a second hardness that is less than the first hardness.

3. A catheter as claimed in claim 1, wherein
the radiopaque marker is formed from a noble metal.

4. A catheter as claimed in claim 1, wherein
the radiopaque marker defines a distal end that is one of aligned with the distal end of the catheter body, proximal of the distal end of the catheter body, and distal of the distal end of the catheter body.

5. A catheter as claimed in claim 1, wherein
the radiopaque marker defines a distal end that is proximal of the distal end of the catheter body; and
a portion of the tip is located within the lumen.

6. A catheter as claimed in claim 1, further comprising:
an abutment located within the lumen proximal of the radiopaque marker.

7. A catheter, comprising;
a tubular catheter body formed from a first material having a first hardness and including a distal portion, a distal end and a surface that defines a lumen that extends to the distal end;
a radiopaque marker carried within the lumen inward of the surface that defines the lumen; and
a non-metal tip, formed from a silicone adhesive having a second hardness that is less than the first hardness, that is bonded to the distal end of the catheter body.

8. A catheter as claimed in claim 7, further comprising:
an abutment located within the lumen proximal of the radiopaque marker.

9. A catheter as claimed in claim 7, wherein
the radiopaque marker is formed from a noble metal.

10. A catheter as claimed in claim 7, wherein
the radiopaque marker has a solid cylinder shape.

11. A catheter as claimed in claim 7, wherein
the radiopaque marker defines a distal end that proximal of the distal end of the catheter body; and
a portion of the tip is located within the lumen.

12. A catheter, comprising:
a tubular catheter body defining a distal portion, a distal end and a lumen that extends to the distal end;
a radiopaque marker carried within the lumen; and
a non-metal tip that is bonded to distal end of the catheter body;
wherein
the radiopaque marker defines a distal end that is proximal of the distal end of the catheter body; and
the radiopaque marker is at least substantially encased in a silicone shell.

13. A catheter as claimed in claim 12, further comprising:
an abutment located within the lumen proximal of the radiopaque marker.

14. A catheter as claimed in claim 12, wherein
the radiopaque marker is formed from a noble metal.

15. A catheter as claimed in claim 12, wherein
the tip is formed a silicone adhesive.

16. A catheter as claimed in claim 12, wherein
the tip is secured to the catheter body with a silicone adhesive.

17. A catheter, comprising:
a tubular catheter body defining a size and a shape that facilitates insertion into an intrathecal space and including a distal portion, a distal end and a surface that defines a lumen with an inner diameter that extends to the distal end;

a radiopaque marker, defining a solid cylinder shape and an outer diameter that is greater than or equal to the inner diameter of the lumen, carried within the lumen;

a non-metal tip that is formed from different material than the catheter body; and a bond that secures the non-metal tip to the distal end of the catheter body.

18. A catheter as claimed in claim 17, further comprising:

an abutment, defining a solid cylinder shape, located within the lumen such that the abutment is between the radiopaque marker and the non-metal tip.

19. A catheter as claimed in claim 17, wherein the bond comprises a bond between silicone polymers.

20. A catheter as claimed in claim 17, wherein the catheter body is formed from a first material having a first hardness; and the non-metal tip is formed from a second material having a second hardness that is less than the first hardness.

21. A catheter as claimed in claim 17, wherein the radiopaque marker is formed from a noble metal.

22. A catheter as claimed in claim 17, wherein the catheter body is formed from a thermoset material; and the tip is formed from a thermoset material.

\* \* \* \* \*